(12) United States Patent
Gleich et al.

(10) Patent No.: US 9,357,943 B2
(45) Date of Patent: Jun. 7, 2016

(54) ARRANGEMENT FOR IMAGING AN OBJECT INCLUDING A VESSEL USING MAGNETIC PARTICLE IMAGING

(75) Inventors: Bernhard Gleich, Hamburg (DE); Juergen Weizenecker, Stutensee (DE)

(73) Assignee: Koninklijke Philips N.V., Eindhoven (NL)

( * ) Notice: Subject to any disclaimer, the term of this patent is extended or adjusted under 35 U.S.C. 154(b) by 468 days.

(21) Appl. No.: 13/139,747

(22) PCT Filed: Dec. 11, 2009

(86) PCT No.: PCT/IB2009/055680
§ 371 (c)(1),
(2), (4) Date: Jun. 15, 2011

(87) PCT Pub. No.: WO2010/070558
PCT Pub. Date: Jun. 24, 2010

(65) Prior Publication Data
US 2012/0035456 A1 Feb. 9, 2012

(30) Foreign Application Priority Data
Dec. 19, 2008 (EP) .................................... 08172339

(51) Int. Cl.
*A61B 5/055* (2006.01)
*A61B 5/05* (2006.01)
*A61B 5/02* (2006.01)
*G01R 33/12* (2006.01)
*A61B 5/00* (2006.01)

(52) U.S. Cl.
CPC ............... *A61B 5/05* (2013.01); *A61B 5/02007* (2013.01); *A61B 5/0515* (2013.01); *G01R 33/1269* (2013.01); *A61B 5/7242* (2013.01)

(58) Field of Classification Search
CPC ............. G01R 33/445; G01R 33/1269; A61B 2019/5236; A61B 5/05; A61B 5/02007; A61B 5/0515; A61B 5/7242
See application file for complete search history.

(56) References Cited

U.S. PATENT DOCUMENTS
2006/0062447 A1 3/2006 Rinck et al.
2008/0192887 A1 8/2008 Weese et al.

FOREIGN PATENT DOCUMENTS
DE 10151778 A1 10/2001
WO 2006064392 A2 6/2006

OTHER PUBLICATIONS
By S. Worz et al.; "Segmentation and Quantification of Human Vessels Using a 3-D Cylindrical Intensity Model" IEEE Transactions on Image Processing, vol. 16, No. 8 Aug. 1, 2007, pp. 1994-2004.

*Primary Examiner* — Mark Remaly

(57) ABSTRACT

An arrangement (10) and a method for imaging an object including a vessel (400), using magnetic particle imaging is provided. An image of the vessel (400) is reconstructed based on a known concentration of the magnetic particles (100) within the vessel (400) and on vessel tree data about the progression of said vessel (400). The reconstruction comprises defining cylinder elements (440) around an approximated image and stepwise and separately adapting the radii of the cylinder elements by integrating over the signal intensity of the cylinder elements, wherein the radii are adapted such that the integrated signal intensity over the cylinder elements equals the intensity expected from the known concentration of the magnetic particles in the vessel.

10 Claims, 6 Drawing Sheets

ARRANGEMENT FOR IMAGING AN OBJECT INCLUDING A VESSEL USING MAGNETIC PARTICLE IMAGING

FIELD OF THE INVENTION

The present invention relates to an arrangement, a method and a computer program using the principle of Magnetic Particle Imaging (MPI) for imaging an object including a vessel, within which magnetic particles are present and which is placed in a region of action.

BACKGROUND OF THE INVENTION

The general principle of MPI is known from German patent application DE 101 51 778 A1. In the arrangement described in that publication, first of all a magnetic selection field having a spatial distribution of the magnetic field strength is generated such that a first sub-zone having a relatively low magnetic field strength and a second sub-zone having a relatively high magnetic field strength are formed in the examination zone. The position in space of the sub-zones in the examination zone is then shifted, so that the magnetization of the particles in the examination zone changes locally. Signals are recorded which are dependent on the magnetization in the examination zone, which magnetization has been influenced by the shift in the position in space of the sub-zones, and information concerning the spatial distribution of the magnetic particles in the examination zone is extracted from these signals, so that an image of the examination zone can be formed. Such an arrangement has the advantage that it can be used to examine arbitrary examination objects—e. g. human bodies—in a non-destructive manner and without causing any damage and with a high spatial resolution, both close to the surface and remote from the surface of the examination object.

A similar arrangement and method is known from Gleich, B. and Weizenecker, J. (2005), "Tomographic imaging using the nonlinear response of magnetic particles" in nature, vol. 435, pp. 1214-1217. The arrangement and method for MPI described in that publication takes advantage of the non-linear magnetization curve of small magnetic particles.

The application of such MPI arrangements in cardiac imaging systems has emerged as a promising market. Especially the imaging of coronaries has shown to become an important issue. In known arrangements, it has been so far difficult to image the progression of a vessel with a high resolution image. In particular for the diagnosis of a stenosis in coronary arteries, MPI arrangements of the prior art have not been ideally applicable, since an adequate solution for reconstructing a high-resolution image of a vessel from the acquired detection signals of MPI systems of the prior art is not known so far. While known MPI systems have enough temporal resolution, the spatial resolution with currently available tracer material is not sufficient to diagnose a stenosis directly.

SUMMARY OF THE INVENTION

It is therefore an object of the present invention to further develop MPI arrangements of the prior art in order to establish an applicable solution for high-resolution imaging of objects within vessels, in particular for the diagnosis of a stenosis in coronary arteries. Thereby, it is an object to provide an arrangement and/or a method which is able to transfer acquired quantitative MPI data into a measure of the diameter of an artery and the volume flow rate of the blood through this artery.

The object is achieved according to the present invention by an arrangement for imaging an object including a vessel, within which magnetic particles are present and which is placed in a region of action, comprising:

selection means for generating a magnetic selection field having a pattern in space of its magnetic field strength such that a first sub-zone having a low magnetic field strength and a second sub-zone having a higher magnetic field strength are formed in the region of action, drive means for changing the position in space of the two sub-zones in the region of action by means of a magnetic drive field so that the magnetization of the magnetic material changes locally, receiving means for acquiring detection signals, which detection signals depend on the magnetization in the region of action, which magnetization is influenced by the change in the position in space of the first and second sub-zone, processing means for reconstructing an image of the vessel based on a known concentration of the magnetic particles within the vessel and on vessel tree data about the progression of said vessel, said processing means comprising:
a) transformation means for transforming the signal intensity of the acquired detection signals into an approximated image of a segment of interest of the vessel based on said vessel tree data,
b) defining means for defining a cylinder, comprising cylinder elements, around said approximated image,
c) adapting means for stepwise and separately adapting the radii of said cylinder elements by integrating over the signal intensity of said cylinder elements, wherein the radii are adapted such that the integrated signal intensity over said cylinder elements equals the intensity expected from the known concentration of the magnetic particles in the vessel,
d) reconstruction means for reconstructing an improved image by transforming the signal intensity of the acquired detection signals based on the adapted radii of said cylinder elements,
e) iteration means for repeating the steps performed by the defining means, adapting means and reconstruction means until a predefined condition is fulfilled, wherein said improved image is used as approximated image in the step performed by the defining means, and
f) displaying means for displaying said reconstructed image as cylinders with the determined radii.

The object is furthermore achieved according to the present invention by a method for imaging an object including a vessel, within which magnetic particles are present and which is placed in a region of action, comprising the steps of:

generating a magnetic selection field having a pattern in space of its magnetic field strength such that a first sub-zone having a low magnetic field strength and a second sub-zone having a higher magnetic field strength are formed in the region of action, changing the position in space of the two sub-zones in the region of action by means of a magnetic drive field so that the magnetization of the magnetic material changes locally, acquiring detection signals, which detection signals depend on the magnetization in the region of action, which magnetization is influenced by the change in the position in space of the first and second sub-zone, reconstructing an image of the vessel based on a known concentration of the magnetic particles within the vessel and on vessel tree data about the progression of said vessel, said step of reconstructing an image comprising the steps:

a) transforming the signal intensity of the acquired detection signals into an approximated image of a segment of interest of the vessel based on said vessel tree data, b) defining a cylinder, comprising cylinder elements, around said approximated image, c) stepwise and separately adapting the radii of said cylinder elements by integrating over the signal intensity of said cylinder elements, wherein the radii are adapted such that the integrated signal intensity over said cylinder elements equals the intensity expected from the known concentration of the magnetic particles in the vessel, d) reconstructing an improved image by transforming the signal intensity of the acquired detection signals based on the adapted radii of said cylinder elements, e) repeating steps b) to d) until a predefined condition is fulfilled, wherein said improved image is used as approximated image in step b), and f) displaying said reconstructed image as cylinders with the determined radii.

The object is furthermore achieved according to the present invention by a computer program comprising program code means for causing a computer to control an arrangement as claimed in claim 1 to carry out the steps of the method as claimed in claim 5 when said computer program is carried out on the computer.

The presented invention makes use of the ability of an MPI system to quantitatively measure the local concentration of magnetic material in a region of action. In the described application of stenosis detection, the concentration of a tracer, which is injected in the examined object prior to the application, can therefore be evaluated in the region of action. On the other hand, the concentration $\vec{c}$ of the magnetic particles in the blood can be calculated based on the amount of the tracer and the concentration of the magnetic particles therein. Since the magnetic tracer is applied in form of a bolus injection, only the examined vessels create a signal in response to the magnetic field produced by the MPI system. The concentration $\vec{c}$ of the magnetic particles in the blood can be therefore received by taking the highest concentration measured in the imaging data set after performing a temporal and spatial average determination.

Using this information, it is therefore possible to utilize the acquired signal intensity as a measure for the diameter of the examined vessel and the volume flow rate of the blood. This is performed by an image reconstruction process.

In this image reconstruction process, it is generally assumed that the "forward problem" is already known. That means, that an expected signal $\vec{S}_e$ can be determined from the known concentration $\vec{c}$ of the magnetic particles. Since in an MPI system as proposed by the present invention a linear problem approach can be used as a reliable approximation, the expected signal $\vec{S}_e$ can be determined as follows:

$\vec{S}_e = G \cdot \vec{c}$; with G being the discretized system function (system matrix).

This system function G therefore describes the relationship between the concentration $\vec{c}$ of the magnetic particles at every location $\vec{x}$ and the expected signal $\vec{S}_e$. The system function G itself can be determined by the use of a delta probe which is positioned at all locations $\vec{x}$ in the examination area. This process is already explained in detail in WO 2006/064392 A2.

The task of the imaging reconstruction process is then to determine a concentration $\vec{c}$ of the magnetic particles from a measured system answer $\vec{S}_m$, so that the expression $\|\vec{S}_m - \vec{S}_e\| = \|\vec{S}_m - G \cdot \vec{c}\|$ is minimized. This expression is therefore minimized if the measured system answer $\vec{S}_m$ equals the expected signal $\vec{S}_e$ for a determined $\vec{c}$.

The basic principles of a reconstruction process are already known and described in detail in WO 2006/064392 A2.

The method proposed according to the present invention can be stepwise explained as follows:

In a first step, the acquired signal intensity is transferred into an approximated image which consists of a plurality of voxels. Nevertheless, the quality of this initially produced image is relatively weak due to the influence of noise. The approximated image is therefore stepwise improved by integrating over cylinder elements which are defined around the surrounding lines of the approximated image. Within this integration, the method is set that the signal intensity inside the cylinder elements is equal to the known, respectively expected signal intensity and the signal intensity outside the cylinder elements equals zero.

The radii and lengths of each cylinder element are therefore stepwise and individually adapted within an imaging reconstruction process as explained above until the integrated signal intensity over the cylinder element is equivalent to the value expected, respectively calculated based on the known concentration of the magnetic particles in the blood. Using these adapted cylinder elements, an improved image with a now better resolution is reconstructed.

The mentioned process is then repeated until a predefined condition is fulfilled, wherein the improved image is used as approximated image in the first step of the iteration process so that the process starts every time with an improved image which is then further refined.

The imaging reconstruction can thereby be mathematically performed either in the voxel space or in the space of the cylindrical elements. If the reconstruction is performed in the mathematical space of the cylindrical elements, $\vec{c}$ does not define the concentration of the magnetic particles in each voxel, but rather defines the concentration, the location and the shape of the cylindrical elements. The optimization is then directly preformed by varying the cylinder elements. Therefore, the number of variables in the above described equations is significantly reduced and the reconstruction is accelerated.

In some cases $\vec{c}$ additionally includes the information of some large voxels, which describe signal parts that are generated in the area outside of the examined vessels. Within the proposed method which can be carried out by the MPI arrangement according to the present invention, it is therefore possible to transform the acquired measurement data into a high-resolution image of the examined vessel respectively the coronary arteries and therefore to directly detect a stenosis within the vessel. Thereby, only a single data set acquired by the MPI system is needed in order to reconstruct the desired image of the examined vessel. This is especially advantageous since the detection of a stenosis within vessels can be accomplished in a fast and comfortable way, and, in case of human patients, the patient is not even exposed to any radiation. The technically possible resolution that can be reached by an arrangement according to the present invention can be even smaller than one voxel.

According to an embodiment of the present invention, it is preferred that the length of the cylinder elements is separately adaptable depending on the desired imaging resolution. Therefore, a very short length of the cylinder elements can be chosen if a high resolution is needed. In this case, the number of cylinder elements which are defined around the approximated image is high and the signal intensity is accurately integrated over only a small volume. However, the data volume is thereby also increased which can lead to longer data processing times. If on the other hand, only a rough approximation of the vessel image is needed, a reconstructed image with a low imaging resolution can be produced by choosing long cylinder elements.

For an optimized process, it is also possible to produce a roughly approximated image in the first step which is then improved by separately adapting the cylinder elements. This means that the local gradient of the signal intensity is measured in the first approximated image, and the length of the cylinder elements is then shortened in the areas where the signal gradient is high. In other words, the resolution is increased where the shape of the imaged vessel strongly changes and therefore a high resolution is needed, i.e. close to a stenosis or parts where the vessel is bent, whereas the resolution in the remaining parts is kept low in order to save data volume and processing time. It is generally desirable to limit the number of cylinder elements, since a too high number of cylinder elements increases the number of control parameters and this again increases the undesired effect of noise. This allows a fast but very accurate and individually adaptable production of the reconstructed image. Additionally it has to be noted, that depending on the application, also other shapes of the elements can be applied instead of cylindrical elements, e.g. elliptical elements.

According to another embodiment of the present invention, it is proposed that the predefined condition is that no significant changes of the radii and positions of the cylinder elements occur. This means that the above mentioned steps performed by the defining means, adapting means and reconstruction means are repeated until no significant changes of the radii and the position of the cylinder elements occur. The image is therefore improved in every iteration until the improvement which can be reached by another iteration tends to be too low so that the iteration is broken up and the reconstructed image is displayed.

In a further preferred embodiment of the present invention, the predefined condition is that the steps performed by the defining means, adapting means and reconstruction means are repeated n-times, wherein n is an integer equal or greater than one. In this embodiment the number of iterations is predefined. This has the advantage that the processing time can be accurately controlled. Especially if only a roughly approximated image is needed the number of iterations can be limited to empirical values which have shown a satisfactory imaging resolution.

In another embodiment of the present invention, it is preferred that the adapting means are configured to introduce a first error term to the signal if the integrated signal intensity over said cylinder elements differs from the known concentration of the magnetic particles in the vessel.

Furthermore, it is preferred according to an embodiment of the present invention that the adapting means are configured to introduce a second error term to the signal if the signal intensity outside of the cylinder elements is greater than zero. By introducing these to two error terms, the convergence of the iteration is additionally improved.

According to a further embodiment, the adapting means are configured to adapt the parameters of the first and the second error term at least once before the predefined condition is fulfilled. In other words, the parameters of the two error terms can be recalculated, respectively narrowed during the iteration. This enables an even faster convergence of the iteration.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
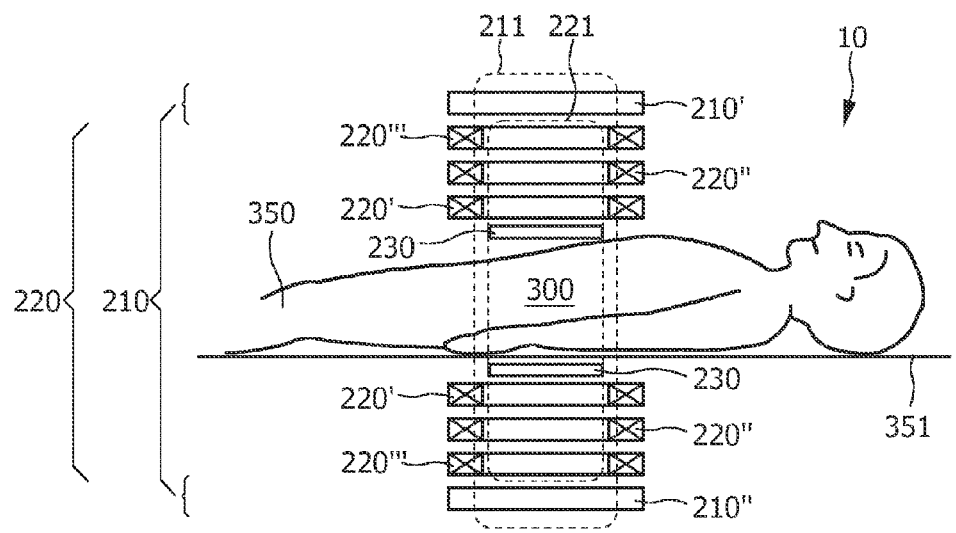
FIG. 1 shows a schematic view of the principle layout of a magnetic particle imaging (MPI) arrangement.

FIG. 1 shows an arbitrary object to be examined by means of a MPI arrangement 10. The reference numeral 350 in FIG. 1 denotes an object, in this case a human or animal patient, who is arranged on a patient table 351, only part of the top of which is shown. Prior to the application of the method according to the present invention, magnetic particles 100 (not shown in FIG. 1) are arranged in a region of action 300 of the inventive arrangement 10. Especially prior to a therapeutical and/or diagnostical treatment of, for example, a tumor, the magnetic particles 100 are positioned in the region of action 300, e.g. by means of a liquid (not shown) comprising the magnetic particles 100 which is injected into the body of the patient 350.

Figure 2:
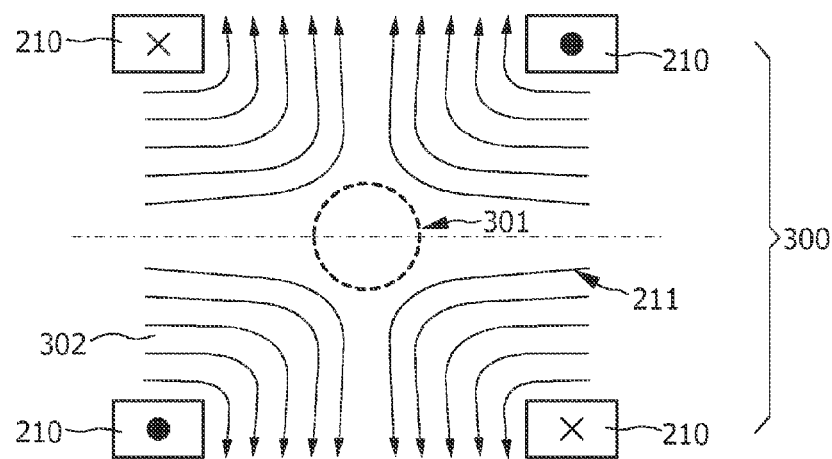
FIG. 2 shows an example of the principle field line pattern produced by an MPI arrangement.

As an example of an embodiment of the present invention, an arrangement 10 is shown in FIG. 2 comprising a plurality of coils forming a selection means 210 whose range defines the region of action 300 which is also called the region of treatment 300. For example, the selection means 210 is arranged above and below the patient 350 or above and below the table top. For example, the selection means 210 comprise a first pair of coils 210', 210", each comprising two identically constructed windings 210' and 210" which are arranged coaxially above and below the patient 350 and which are traversed by equal currents, especially in opposed directions. The first coil pair 210', 210" together are called selection means 210 in the following. Preferably, direct currents are used in this case. The selection means 210 generate a magnetic selection field 211 which is in general a gradient magnetic field which is represented in FIG. 2 by the field lines. It has a substantially constant gradient in the direction of the (e.g. vertical) axis of the coil pair of the selection means 210 and reaches the value zero in a point on this axis. Starting from this field-free point (not individually shown in FIG. 2), the field strength of the magnetic selection field 211 increases in all three spatial directions as the distance increases from the field-free point. In a first sub-zone 301 or region 301 which is denoted by a dashed line around the field-free point the field strength is so small that the magnetization of particles 100 present in that first sub-zone 301 is not saturated, whereas the magnetization of particles 100 present in a second sub-zone 302 (outside the region 301) is in a state of saturation. The field-free point or first sub-zone 301 of the region of action 300 is preferably a spatially coherent area; it may also be a punctiform area or else a line or a flat area. In the second sub-zone 302 (i.e. in the residual part of the region of action 300 outside of the first sub-zone 301) the magnetic field strength is sufficiently strong to keep the particles 100 in a state of saturation. By changing the position of the two sub-zones 301, 302 within the region of action 300, the (overall) magnetization in the region of action 300 changes. By measuring the magnetization in the region of action 300 or a physical parameters influenced by the magnetization, information about the spatial distribution of the magnetic particles in the region of action can be obtained. In order to change the relative spatial position of the two sub-zones 301, 302 in the region of action 300, a further magnetic field, the so-called magnetic drive field 221, is superposed to the selection field 211 in the region of action 300 or at least in a part of the region of action 300.

Figure 3:
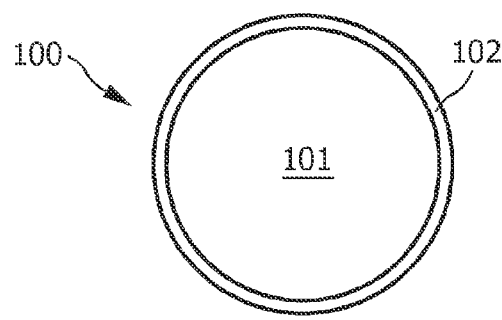
FIG. 3 shows an enlarged view of a magnetic particle present in the region of action.

FIG. 3 shows an example of a magnetic particle 100 of the kind used together with an arrangement 10 of the present invention. It comprises for example a spherical substrate 101, for example, of glass which is provided with a soft-magnetic layer 102 which has a thickness of, for example, 5 nm and consists, for example, of an iron-nickel alloy (for example, Permalloy). This layer may be covered, for example, by means of a coating layer 103 which protects the particle 100 against chemically and/or physically aggressive environments, e.g. acids. The magnetic field strength of the magnetic selection field 211 required for the saturation of the magnetization of such particles 100 is dependent on various parameters, e.g. the diameter of the particles 100, the used magnetic material for the magnetic layer 102 and other parameters.

In the case of e.g. a diameter of 10 µm, a magnetic field of approximately 800 A/m (corresponding approximately to a flux density of 1 mT) is then required, whereas in the case of a diameter of 100 µm a magnetic field of 80 A/m suffices. Even smaller values are obtained when a coating 102 of a material having a lower saturation magnetization is chosen or when the thickness of the layer 102 is reduced.

For further details of the preferred magnetic particles 100, the corresponding parts of DE 10151778 are hereby incorporated by reference, especially paragraphs 16 to 20 and paragraphs 57 to 61 of EP 1304542 A2 claiming the priority of DE 10151778.

The size of the first sub-zone 301 is dependent on the one hand on the strength of the gradient of the magnetic selection field 211 and on the other hand on the field strength of the magnetic field required for saturation. For a sufficient saturation of the magnetic particles 100 at a magnetic field strength of 80 A/m and a gradient (in a given space direction) of the field strength of the magnetic selection field 211 amounting to 160 $10^3$ A/m2, the first sub-zone 301 in which the magnetization of the particles 100 is not saturated has dimensions of about 1 mm (in the given space direction).

When a further magnetic field—in the following called a magnetic drive field 221 is superposed on the magnetic selection field 211 (or gradient magnetic field 211) in the region of action 300, the first sub-zone 301 is shifted relative to the second sub-zone 302 in the direction of this magnetic drive field 221; the extent of this shift increases as the strength of the magnetic drive field 221 increases. When the superposed magnetic drive field 221 is variable in time, the position of the first sub-zone 301 varies accordingly in time and in space. It is advantageous to receive or to detect signals from the magnetic particles 100 located in the first sub-zone 301 in another frequency band (shifted to higher frequencies) than the frequency band of the magnetic drive field 221 variations. This is possible because frequency components of higher harmonics of the magnetic drive field 221 frequency occur due to a change in magnetization of the magnetic particles 100 in the region of action 300 as a result of the non-linearity of the magnetization characteristics.

In order to generate these magnetic drive fields 221 for any given direction in space, there are provided three further coil pairs, namely a second coil pair 220', a third coil pair 220" and a fourth coil pair 220''' which together are called drive means 220 in the following. For example, the second coil pair 220' generates a component of the magnetic drive field 221 which extends in the direction of the coil axis of the first coil pair 210', 210" or the selection means 210, i.e. for example vertically. To this end the windings of the second coil pair 220' are traversed by equal currents in the same direction. The effect that can be achieved by means of the second coil pair 220' can in principle also be achieved by the superposition of currents in the same direction on the opposed, equal currents in the first coil pair 210', 210", so that the current decreases in one coil and increases in the other coil. However, and especially for the purpose of a signal interpretation with a higher signal to noise ratio, it may be advantageous when the temporally constant (or quasi constant) selection field 211 (also called gradient magnetic field) and the temporally variable vertical magnetic drive field are generated by separate coil pairs of the selection means 210 and of the drive means 220.

The two further coil pairs 220", 220''' are provided in order to generate components of the magnetic drive field 221 which extend in a different direction in space, e.g. horizontally in the longitudinal direction of the region of action 300 (or the patient 350) and in a direction perpendicular thereto. If third and fourth coil pairs 220", 220''' of the Helmholtz type (like the coil pairs for the selection means 210 and the drive means 220) were used for this purpose, these coil pairs would have to be arranged to the left and the right of the region of treatment or in front of and behind this region, respectively. This would affect the accessibility of the region of action 300 or the region of treatment 300. Therefore, the third and/or fourth magnetic coil pairs or coils 220", 220''' are also arranged above and below the region of action 300 and, therefore, their winding configuration must be different from that of the second coil pair 220'. Coils of this kind, however, are known from the field of magnetic resonance apparatus with open magnets (open MRI) in which an radio frequency (RF) coil pair is situated above and below the region of treatment, said RF coil pair being capable of generating a horizontal, temporally variable magnetic field. Therefore, the construction of such coils need not be further elaborated herein.

The arrangement 10 according to the present invention further comprise receiving means 230 that are only schematically shown in FIG. 1. The receiving means 230 usually comprise coils that are able to detect the signals induced by magnetization pattern of the magnetic particles 100 in the region of action 300. Coils of this kind, however, are known from the field of magnetic resonance apparatus in which e.g. a radio frequency (RF) coil pair is situated around the region of action 300 in order to have a signal to noise ratio as high as possible. Therefore, the construction of such coils need not be further elaborated herein.

In an alternative embodiment for the selection means 210 shown in FIG. 1, permanent magnets (not shown) can be used to generate the gradient magnetic selection field 211. In the space between two poles of such (opposing) permanent magnets (not shown) there is formed a magnetic field which is similar to that of FIG. 2, that is, when the opposing poles have the same polarity. In another alternative embodiment of the arrangement according to the present invention, the selection means 210 comprise both at least one permanent magnet and at least one coil 210', 210" as depicted in FIG. 2.

The frequency ranges usually used for or in the different components of the selection means 210, drive means 220 and receiving means 230 are roughly as follows: The magnetic field generated by the selection means 210 does either not vary at all over the time or the variation is comparably slow, preferably between approximately 1 Hz and approximately 100 Hz. The magnetic field generated by the drive means 220 varies preferably between approximately 25 kHz and approximately 100 kHz. The magnetic field variations that the receiving means are supposed to be sensitive are preferably in a frequency range of approximately 50 kHz to approximately 10 MHz.

Figure 4A:
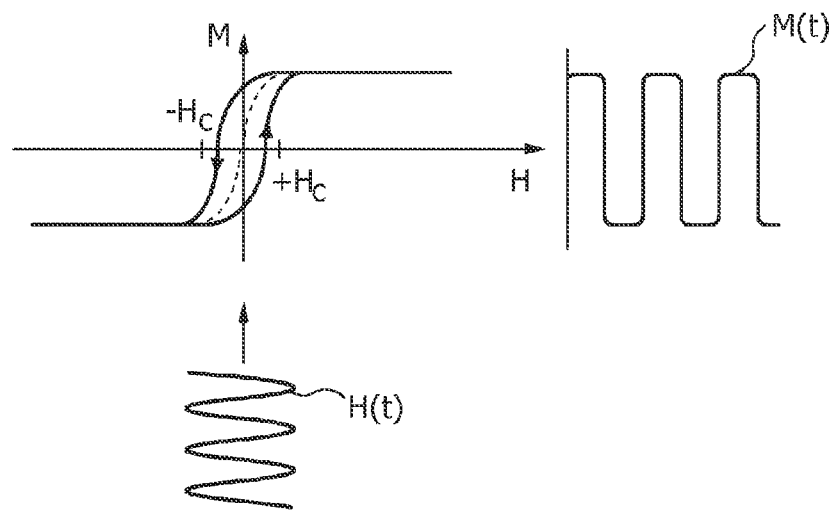
FIGS. 4a and 4b show the magnetization characteristics of such particles.
Figure 4B:
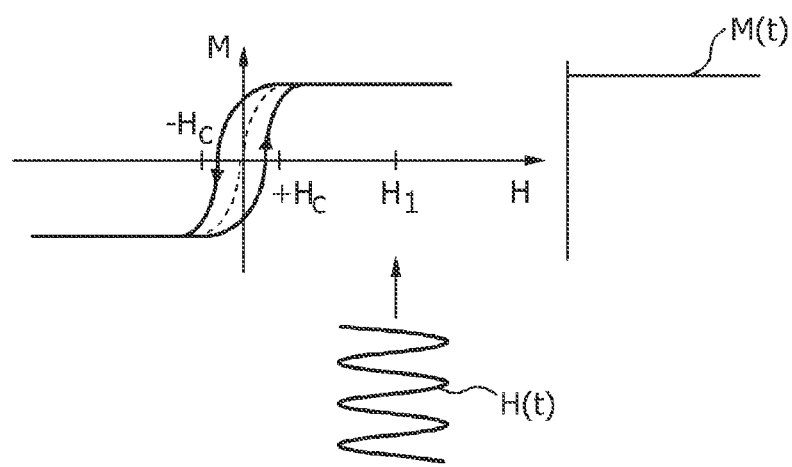

FIGS. 4a and 4b show the magnetization characteristic, that is, the variation of the magnetization M of a particle 100 (not shown in FIGS. 4a and 4b) as a function of the field strength H at the location of that particle 100, in a dispersion with such particles. It appears that the magnetization M no longer changes beyond a field strength $+H_c$ and below a field strength $-H_c$, which means that a saturated magnetization is reached. The magnetization M is not saturated between the values $+H_c$ and $-H_c$.

FIG. 4a illustrates the effect of a sinusoidal magnetic field H(t) at the location of the particle 100 where the absolute values of the resulting sinusoidal magnetic field H(t) (i.e. "seen by the particle 100") are lower than the magnetic field strength required to magnetically saturate the particle 100, i.e. in the case where no further magnetic field is active. The magnetization of the particle 100 or particels 100 for this condition reciprocates between its saturation values at the rhythm of the frequency of the magnetic field H(t). The resultant variation in time of the magnetization is denoted by the reference M(t) on the right hand side of FIG. 4a. It appears that the magnetization also changes periodically and that the magnetization of such a particle is periodically reversed.

The dashed part of the line at the centre of the curve denotes the approximate mean variation of the magnetization M(t) as a function of the field strength of the sinusoidal magnetic field H(t). As a deviation from this centre line, the magnetization extends slightly to the right when the magnetic field H increases from $-H_c$ to $+H_c$ and slightly to the left when the magnetic field H decreases from $+H_c$ to $-H_c$. This known effect is called a hysteresis effect which underlies a mechanism for the generation of heat. The hysteresis surface area which is formed between the paths of the curve and whose shape and size are dependent on the material, is a measure for the generation of heat upon variation of the magnetization.

FIG. 4b shows the effect of a sinusoidal magnetic field H(t) on which a static magnetic field $H_1$ is superposed. Because the magnetization is in the saturated state, it is practically not influenced by the sinusoidal magnetic field H(t). The magnetization M(t) remains constant in time at this area. Consequently, the magnetic field H(t) does not cause a change of the state of the magnetization.

Figure 5:
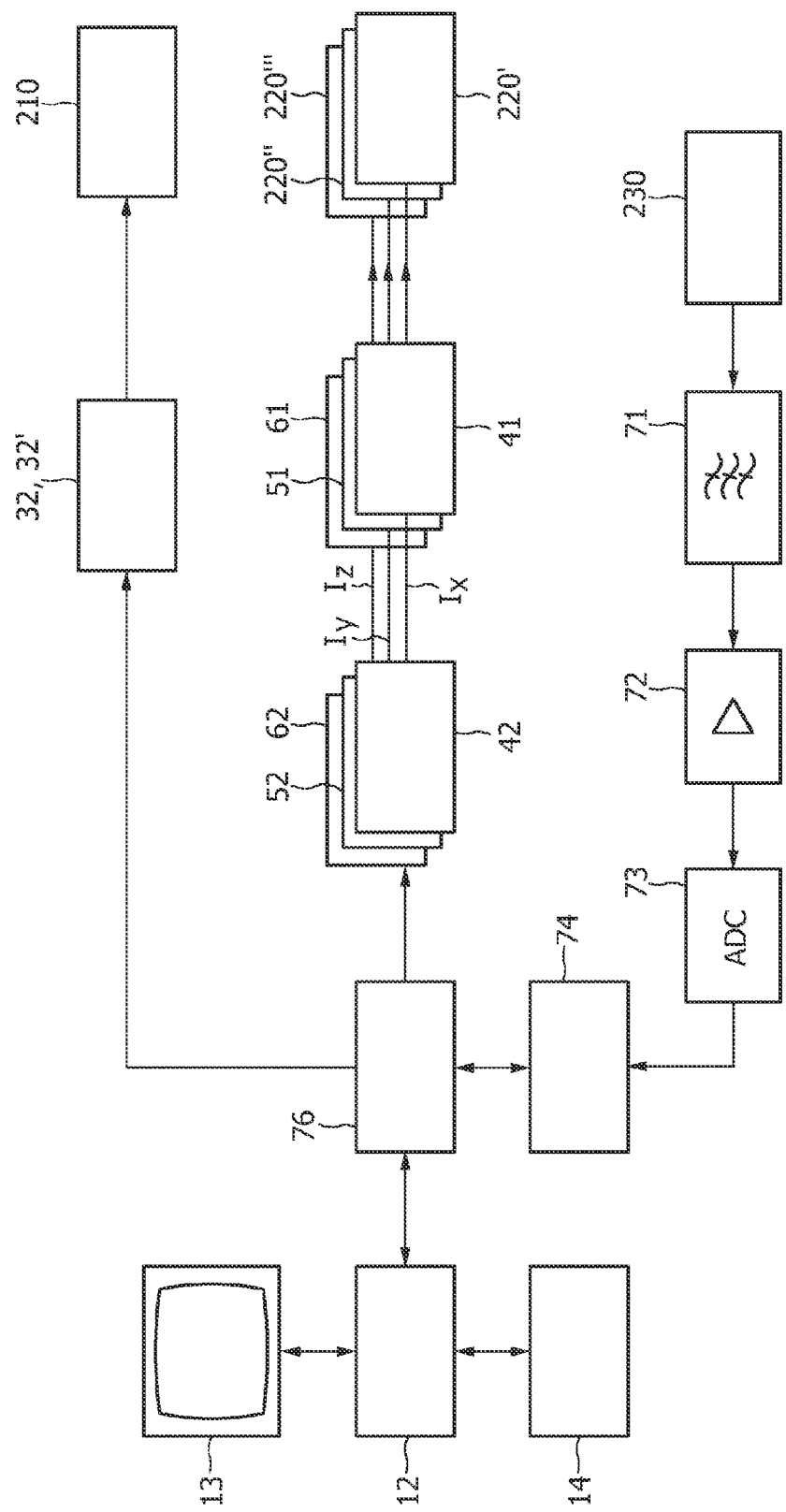
FIG. 5 shows a block diagram of the arrangement according to the present invention.

FIG. 5 shows a block diagram of the apparatus 10 shown in FIG. 1. The selection means 210 is shown schematically in FIG. 5. Preferably, the selection means 210 are provided with three magnetic selection field generation means, in particular either coils, permanent magnets or a combination of coils and permanent magnets. Said three magnetic selection field generation means are preferably arranged such that for each spatial direction one magnetic selection field generation means is provided. If in an embodiment coil pairs are provided as magnetic selection field generation means, the coil pairs are supplied with a DC current from a controllable current source 32, said current source 32 being controlled by the control means 76. The control means 76 is in turn connected to a computer 12 which is coupled to a monitor 13 for displaying the distribution of magnetic particles in the examination area and an input unit 14, for example a keyboard.

The coil pairs (second magnetic means) 220', 220", 220''' are connected to current amplifiers 41, 51, 61, from which they receive their currents. The current amplifiers 41, 51, 61 are in turn in each case connected to an AC current source 42, 52, 62 which defines the temporal course of the currents Ix, Iy, Iz to be amplified. The AC current sources 42, 52, 62 are controlled by the control means 76.

The receiving coil (receiving means) is also shown schematically in FIG. 5. The signals induced in the receiving coil 230 are fed to a filter unit 71, by means of which the signals are filtered. The aim of this filtering is to separate measured values, which are caused by the magnetization in the examination area which is influenced by the change in position of the two part-regions (301, 302), from other, interfering signals. To this end, the filter unit 71 may be designed for example such that signals which have temporal frequencies that are smaller than the temporal frequencies with which the coil pairs 220', 220", 220''' are operated, or smaller than twice these temporal frequencies, do not pass the filter unit 71. The signals are then transmitted via an amplifier unit 72 to an analog/digital converter 73 (ADC). The digitalized signals produced by the analog/digital converter 73 are fed to a processing means 74, which reconstructs the spatial distribution of the magnetic particles from these signals and the respective position which the first part-region 301 of the first magnetic field in the examination area assumed during receipt of the respective signal and which the image processing means 74 obtains from the control means 76. The quantitatively measured local concentration of the magnetic material in the region of action is transformed in the processing means 74 into a reconstructed image.

The method according to the present invention proposes an iterative process which is carried out by said processing means 74 in order to use the acquired signal intensity as a measure for flux and diameter of an examined vessel, and therefore to transform the acquired measurement data into a high-resolution image. This reconstructed high-resolution image data is finally transmitted via the control means 76 to the computer 12, which displays it on the monitor 13. It has to be noted that, according to the present invention, said processing means 74 are included in the computer wherein the proposed iteration method can be supported respectively carried out by a computer program.

Figure 6:
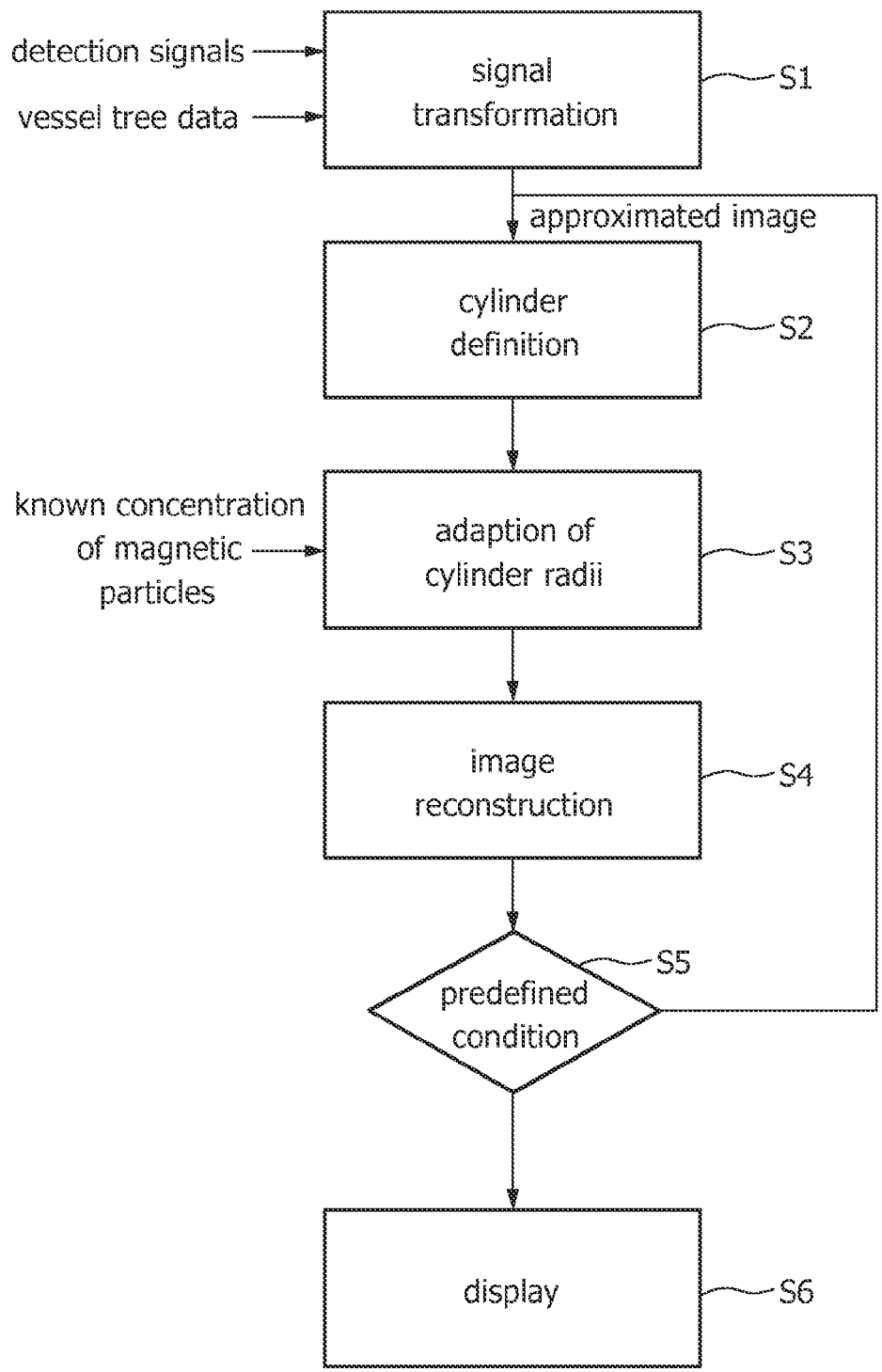
FIG. 6 shows a block diagram of the method according to the present invention.
Figure 7:
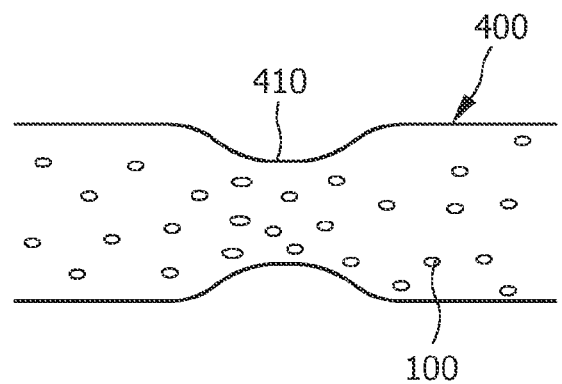
FIG. 7 shows a schematic view a segment of interest of a vessel within which magnetic particles are present.

The detailed method which is carried out by said processing means 74 is shown in FIG. 6. The proposed method is designed in particular for the application of imaging a stenosis 410 within a coronary artery. An example of such a vessel 400 under examination, which contains magnetic particles 100, is shown in FIG. 7. In a first step S1 of the method, the signal intensity of the detection signals acquired by the receiving coil 230 is transformed into an approximated image 420 of the vessel 400. Since the magnetic tracer is applied in form of a bolus injection, only the examined vessels 400 create a signal in response to the produced magnetic field whereas areas outside of the vessel 400 do not contribute to the signal. The signal intensity is therefore integrated around a fixed, predefined area of a known vessel tree. This vessel tree data can be a first estimation of the progression of the vessel 400 which is to be imaged and is used as input data for the signal transformation. The approximated image 420 which is produced in the first step S1 of the method is, for instance, a bright-dark image showing dark areas 425 for areas with high signal intensity and bright areas 430 for areas with low signal intensity. It has to be noted, that the approximated image 420 does not necessarily have to be a bright-dark image, it is also possible to realize said approximated image 420 with two different colors or patterns in order to distinguish areas 425 with high signal intensity from areas 430 with low signal intensity.

Figure 8:
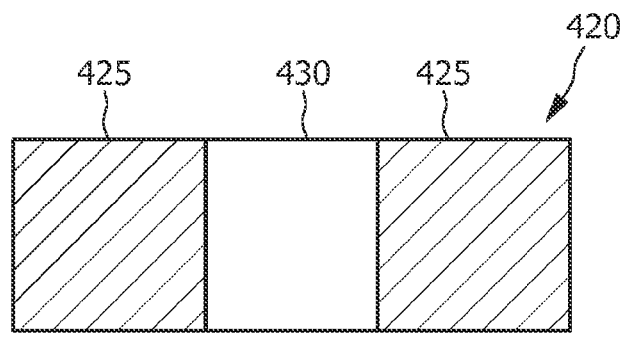
FIG. 8 shows a first approximated image of the segment of interest of the vessel.

Such an approximated image 420 which is produced of the vessel 400, illustrated in FIG. 7, is exemplarily shown in FIG. 8. By comparing the two figures, it can be seen that the area around the stenosis 410 shows a fairly bright picture 430 in FIG. 8 since the signal intensity is in the part where the vessel 400 is constricted also integrated over areas outside of the vessel 400 where no magnetic particles 100 are present. Therefore, noise is also recorded in this part so that the signal intensity is rather low in contrast to the unrestricted parts of the vessel where the signal intensity is only integrated in the inner part of the vessel 400, where magnetic particles 100 are present and a higher signal is recorded. The approximated image 420 (FIG. 8) produced in the first step S1 of the method therefore only gives a rough indication of the position of the stenosis 410.

Figure 9:
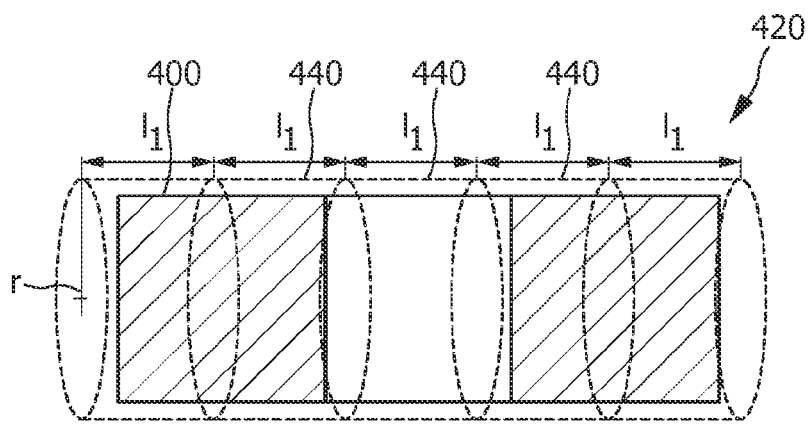
FIG. 9 shows a schematic view of the approximated image including cylinder elements of a constant length around said approximated image.

In the second step S2 of the method shown in FIG. 6, cylinder elements 440 are defined around said approximated image 420. The cylinder elements 440, which are schematically shown in FIG. 9, serve as integration volume in which the signal intensity is integrated in the following steps. After the cylinder elements 440 are defined, the signal intensity is integrated over the volume of each cylinder element 440 separately and the radius r of each cylinder element 440 is individually and stepwise adapted until the signal intensity over each cylinder element 440 is equal and reaches the intensity which is expected from the known concentration of the magnetic particles 100 in the vessel 400 (S3 in FIG. 6). It has to be noted that the concentration of the magnetic particles 100 in the blood is known, respectively can be calculated, based on the amount of the tracer and the concentration of the magnetic particles 100 therein. The concentration of the magnetic particles 100 in the blood can be therefore received by taking the highest concentration measured in the imaging data set after performing a temporal and spatial average determination.

Figure 10:
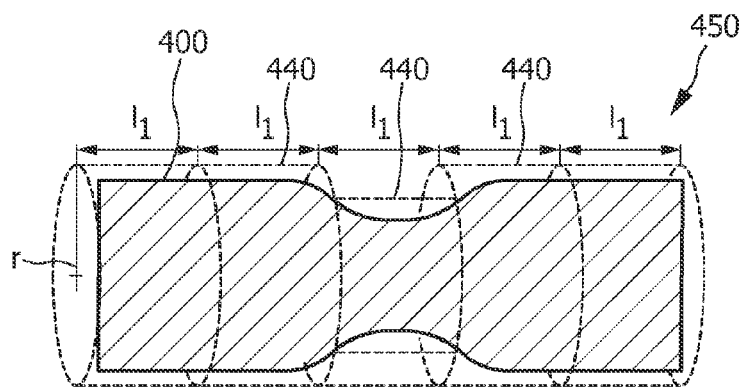
FIG. 10 shows the approximated image including cylinder elements with adapted radii.
Figure 11:
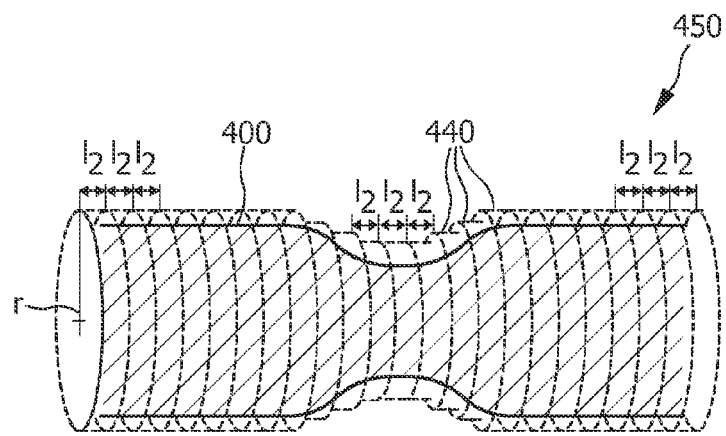
FIG. 11 shows the approximated image including cylinder elements with adapted radii and a smaller, constant length.

In case of the shown example, the cylinder element 440 around the stenosis 410 is therefore decreased until the signal intensity equals the calculated concentration of the magnetic particles 100. This method step S3 is explicitly shown in FIG. 10. Further looking at FIG. 10, it can be seen that the imaging resolution would be in case of fairly long cylinder elements 440 with length $l_1$ (as in FIG. 10) too low since the stenosis then is only surrounded by one single cylinder element 440 which would cause an excursive shape in the reconstructed image. It is therefore preferable to choose a shorter length $l_2$, as shown in FIG. 11, in order to receive a better resolution. Depending on the application and on the necessary resolution, the length of the cylinder elements 440 should be therefore adapted, still keeping in mind that the length should not be chosen too small in order to avoid too long calculation times.

Figure 12:
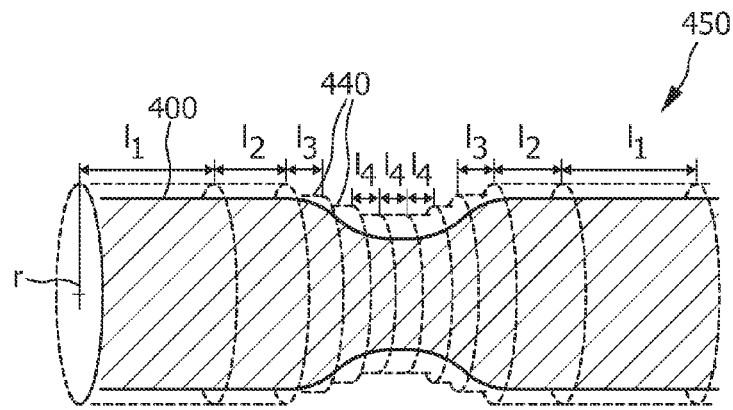
FIG. 12 shows the approximated image including cylinder elements with adapted radii and variable length.

An alternative embodiment is shown in FIG. 12, where the cylinder length is individually adapted. In FIG. 12, therefore cylinder elements 440 of four different lengths $l_1$-$l_4$ are proposed. This means that the local gradient of the signal intensity is measured in the first approximated image 420 and the length of the cylinder elements 440 is then shortened in the areas where the gradient is high. In other words, the resolution is increased where the shape of the imaged vessel 400 strongly changes and therefore a high resolution is needed. This is, for instance, the case close to a stenosis 410 or parts where the vessel 400 is bent. The resolution in the remaining parts is in contrary kept low in order to save data volume and processing time. This allows a fast but very accurate and individually adaptable production of the reconstructed image.

In step S4 (FIG. 6) an improved image 450 is then produced by transforming the signal intensity of the acquired signals based on the adapted radii respectively lengths of the cylinder elements 440 of step S3. Afterwards, the steps S2 to S4 are then repeated until a predefined condition S5 is fulfilled. Within each iteration the improved image 450 is used as approximated image 420 in step S2 and the above described method steps S2 to S4 are carried out again. The predefined condition can thereby either be that the iteration is carried out until no significant changes of the radii and positions of the cylinder elements occur or that the iteration is carried out n-times, where n is an integer greater than one.

After the iteration process is stopped due to the predefined condition, the reconstructed image is displayed on the display 13 in the last step S6. It has to be noted that the user, of course, can repeat this method again or redefine the object area to be examined in order to receive for example a picture of a detailed fraction.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An arrangement for imaging an object including a vessel, within which magnetic particles are present and which is placed in a region of action, comprising:
    selection means for generating a magnetic selection field
        having a pattern in space of a magnetic field strength such that a first sub-zone having a low magnetic field strength and a second sub-zone having a higher magnetic field strength are formed in the region of action;

drive means for changing a position in space of the two sub-zones in the region of action by a magnetic drive field so that a magnetization of the magnetic material changes locally;

receiving means for acquiring detection signals, which detection signals depend on the magnetization in the region of action, which magnetization is influenced by a change in the position in space of the first sub-zone and the second sub-zone; and processing means operably connected to the receiving means for, responsive to the detection signals, reconstructing an image of the vessel based on a known concentration of the magnetic particles within the vessel and on vessel tree data about a progression of said vessel including a) transforming the signal intensity of the acquired detection signals into an approximated image of a segment of interest of the vessel based on said vessel tree data, b) defining a cylinder having cylinder elements around said approximated image, c) stepwise and separately adapting the radii of said cylinder elements by integrating over the signal intensity of said cylinder elements, wherein the radii are adapted such that the integrated signal intensity over said cylinder elements equals the intensity expected from the known concentration of the magnetic particles in the vessel, d) reconstructing an improved image by transforming the signal intensity of the acquired detection signals based on the adapted radii of said cylinder elements, e) repeating the steps b) to d) until a predefined condition is fulfilled, wherein said improved image is used as approximated image in the step b), and f) displaying said improved image as cylinders with the determined radii.

2. An arrangement according to claim 1, wherein a length of the cylinder elements is separately adaptable depending on the desired imaging resolution.

3. An arrangement according to claim 1, wherein the predefined condition is that no significant changes of the radii and positions of the cylinder elements occur.

4. An arrangement according to claim 1, wherein the predefined condition is that the steps b) to d) are repeated n-times, wherein n is an integer equal or greater than one.

5. An arrangement according to claim 1, wherein the processing means is further operable to introduce a first error term to the signal if the integrated signal intensity over said cylinder elements differs from the known concentration of the magnetic particles in the vessel.

6. An arrangement according to claim 1, wherein the processing means is further operable to introduce a second error term to the signal if the signal intensity outside of the cylinder elements is greater than zero.

7. An arrangement according to claim 6, wherein the processing means is further operable to weight the second error term with a function of the distance to the closest cylinder element.

8. An arrangement according to claim 5, wherein the processing means is further operable to adapt the parameters of the first and the second error term at least once before the predefined condition is fulfilled.

9. A method for imaging an object including a vessel, within which magnetic particles are present and which is placed in a region of action, comprising the steps of:

generating a magnetic selection field having a pattern in space of a magnetic field strength such that a first sub-zone having a low magnetic field strength and a second sub-zone having a higher magnetic field strength are formed in the region of action;

changing a position in space of the two sub-zones in the region of action by a magnetic drive field so that a magnetization of the magnetic material changes locally;

acquiring detection signals, which detection signals depend on the magnetization in the region of action, which magnetization is influenced by a change in the position in space of the first sub-zone and the second sub-zone; and reconstructing an image of the vessel based on a known concentration of the magnetic particles within the vessel and on vessel tree data about a progression of said vessel, wherein said step of reconstructing an image includes:

a) transforming the signal intensity of the acquired detection signals into an approximated image of a segment of interest of the vessel based on said vessel tree data, b) defining a cylinder having cylinder elements around said approximated image, c) stepwise and separately adapting the radii of said cylinder elements by integrating over the signal intensity of said cylinder elements, wherein the radii are adapted such that the integrated signal intensity over said cylinder elements equals the intensity expected from the known concentration of the magnetic particles in the vessel, d) reconstructing an improved image by transforming the signal intensity of the acquired detection signals based on the adapted radii of said cylinder elements, e) repeating steps b) to d) until a predefined condition is fulfilled, wherein said improved image is used as approximated image in step b), and f) displaying said reconstructed image as cylinders with the determined radii.

10. A non-transitory computer-readable medium storing a computer program for causing a computer to control an arrangement as claimed in claim 1 to carry out the steps of the method as claimed in claim 9 when said computer program is carried out on the computer.

* * * * *